United States Patent [19]

Mitsuno et al.

[11] Patent Number: 4,767,625
[45] Date of Patent: Aug. 30, 1988

[54] LAMELLA TYPE SINGLE PHASE LIQUID CRYSTAL COMPOSITION AND OIL-BASE COSMETIC COMPOSITIONS USING THE SAME

[75] Inventors: Yuichiro Mitsuno, Sakura; Keiko Nomaguchi, Tokyo; Toshiyuki Suzuki, Ichikawa, all of Japan

[73] Assignee: Kao Corporation, Tokyo, Japan

[21] Appl. No.: 896,457

[22] Filed: Aug. 14, 1986

[30] Foreign Application Priority Data

Sep. 2, 1985 [JP] Japan .................. 60-193426
Oct. 24, 1985 [JP] Japan .................. 60-238165

[51] Int. Cl.$^4$ .............. C09K 19/52; A61K 9/02; A61K 7/00; B01J 13/00
[52] U.S. Cl. .................. 424/95; 252/299.01; 252/122; 252/132; 252/162; 252/173; 252/174.11; 252/174.17; 252/174.19; 252/174.21; 252/174.22; 252/174.23; 252/311; 252/312; 252/315.01; 252/315.1; 252/315.3; 252/315.4; 252/351; 252/356; 424/195.1; 514/54; 514/60; 514/510; 514/511; 514/513; 514/552; 514/718; 514/723; 514/772; 514/844; 514/845; 514/846; 514/847; 514/848; 514/969; 514/970; 514/975
[58] Field of Search .......... 252/299.01, 315.3, 315.1, 252/315.01, 315.4, 311, 312, 351, 356, 122, 132, 162, 173, 174.11, 174.17, 174.19, 174.21, 174.23, 174.22; 424/95, 195.1; 514/54, 60, 723, 772, 844, 845, 510, 552, 846, 511, 718, 847, 513, 848, 969, 970, 975

[56] References Cited

U.S. PATENT DOCUMENTS

4,440,665  4/1984  Mather et al. ............... 252/299.01
4,536,324  8/1985  Fujiwara et al. ............. 252/299.01
4,670,185  6/1987  Fujiwara et al. ............. 252/299.01

FOREIGN PATENT DOCUMENTS

066107  12/1982  European Pat. Off. .
152945   8/1985  European Pat. Off. .
2028864  1/1971  Fed. Rep. of Germany .......... 252/299.01
2419758 10/1979  France .
2502951 10/1982  France .
56-89832  7/1981  Japan ................. 252/299.01
57-70824  5/1982  Japan ................. 252/299.01
59-46123  3/1984  Japan ................. 252/299.01
60-64916  4/1985  Japan ................. 252/299.01

OTHER PUBLICATIONS

"Bericht Forum Cosmeticum 1984: Kosmetische Emulsionen und ihr Verhalten", E. Nurnberg, Seifen-Ole-Fette-Wachse, vol. 111, No. 3, pp. 78–79, Feb. 21, 1985.
"Internal Structure of a Oil-in-Water Emulsions Stabilized with a Cetostearyl Alcohol", S. Fukushima et al, Chemical Abstracts, vol. 101, 1984, pp. 410–411, No. 198632c.

*Primary Examiner*—Teddy S. Gron
*Attorney, Agent, or Firm*—Oblon, Fisher, Spivak, McClelland & Maier

[57] ABSTRACT

A lamella type, single phase liquid crystal composition is prepared from a hydrophilic nonionic surfactant, a water-soluble substance having a hydroxyl group in a molecule thereof, an oil substance, and water.

Oil-base cosmetic compositions including cleansing compositions, massage creams or drugs for external application are incorporated with the liquid crystal.

The compositions are readily washed off simply by water, and exhibit good properties of non-stickiness and long storage stability.

7 Claims, No Drawings

LAMELLA TYPE SINGLE PHASE LIQUID CRYSTAL COMPOSITION AND OIL-BASE COSMETIC COMPOSITIONS USING THE SAME

BACKGROUND OF THE INVENTION (i) Field of the Invention

The present invention relates to a novel lamella type, single phase liquid crystal composition and more particularly to such composition of homogeneous gel, which can be converted into an oily sol of excellent spreadability when water contained therein is evaporated, and is useful as a substrate of cosmetic compositions or drugs for external application which are expected to be readily washed off with water.

(ii) Description of the Prior Art

Cleansing cosmetics and massage cosmetics are widely used in order to remove the skin dirt or make-up cosmetics, or to supply oil to the skin before it is massaged. They are applied to the skin, extended thereon, and finally removed from the skin.

Conventional materials which are commercially available to meet the above purposes are cosmetic compositions containing an oil substance or a water-in-oil type or oil-in-water type emulsion as a substrate. Recently, it has also been reported that a gel of oil-in-surfactant emulsion is applicable as a substrate of cleansing cosmetic compositions (Japanese Patent Application Laid-Open No. 46123/1984).

The use of an oil substance or a water-in-oil emulsion in such compositions is accompanied by a disadvantage in that the applied cleansing or massage cosmetics is hardly removed completely because the continuous phase of the cosmetic compositions consists of oil. Ordinary practice, therefore, is to wipe off the waste cosmetics by tissue paper or the like, then completely wash them out with a facial cleanser or the like. However, the use of tissue paper is not favorable in view that it will also remove the horny cells in the skin, and that the oil transferred to the tissue paper gives sticky feel to fingers. In turn, when an oil-in-water emulsion is used, the waste cosmetics can be washed out without tissue paper but only at an insufficient degree. Especially, the gelled emulsion of oil-in-surfactant type disclosed in Japanese Patent Application Laid-Open No. 46123/1984 has such disadvantages that it gives sticky feel upon use, and that the storage stability is not good because it is a two phase composition, although it has an excellent emulsion dispersibility and can be readily washed out with water.

Under the above circumstances it is still demanded development of a substrate for preparing cleansing compositions, massage creams, drugs for external application or the like which can be readily and completely removed with water without use of tissue paper, will not give sticky feel on use and will have good storage stability.

SUMMARY OF THE INVENTION

The present inventors have made earnest studies for obtaining a substrate which will meet the above requirements and have found that a liquid crystal composition which system lies within the one phase area, prepared from a hydrophilic nonionic surfactant, a water-soluble substance having a hydroxyl group in a molecule thereof, an oil substance, and water is a suitable material for achieving the purpose. The present invention was accomplished based on the above finding.

Accordingly, the present invention provides a lamella type, single phase liquid crystal composition prepared from a hydrophilic nonionic surfactant, a water-soluble substance having a hydroxyl group in a molecule thereof, an oil substance and water. The present invention also provides an oil base cosmetic composition which comprises the liquid crystal composition as a substrate thereof.

DETAILED DESCRIPTION OF THE INVENTION

The hydrophilic nonionic surfactants usable in the present invention are preferably those having an HLB value of 10 or more, which include polyoxyethylene sorbitan fatty acid esters, oxyethylene derivatives of glycerine fatty acid esters, oxyethylene derivatives of propylene glycol fatty acid esters, polyethylene glycol fatty acid esters, polyoxyethylene alkyl ethers, polyoxypropylene alkyl ethers, polyoxyethylene polyoxypropylene alkyl ethers, polyoxyethylene alkylphenyl ethers, polyoxyethylene hydrogenated castor oil and so on having an HLB of 10 or more. They are used solely or in combination of two or more. Incorporation amount is usually from 1 to 30 wt % (hereinafter may be referred to simply as %) based on the total weight and preferably from 10 to 20%. Less amount than 1% will not form a liquid crystal, whereas excess amount than 30% will make the liquid crystal solidified, thus not preferable.

The water-soluble substances having a hydroxyl group in a molecule thereof which are used in this invention include propylene glycol, 1,3-butanediol, dipropylene glycol, glycerine, diglycerine, polyglycerine, trimethylolpropane, erythritol, pentaerythritol, sorbitan, glucose, sorbitol, martitol, saccharose, trehalose, polyoxyethylene methyl glucoside, polyoxypropylene methyl glucoside, polyethylene glycol, ethanol and the like. Among them, glycerine, sorbitol and ethanol are especially preferred. They are used singly or in combination. The incorporation amount of the water-soluble substance may vary according to the intended feel on use, viscosity and the like of the final formulation, and may generally be 1 to 50%, preferably 5 to 15% based on the weight of the total composition.

The above water-soluble substances can be used in combination of two or more. When an ethyleneoxide or propyleneoxide addition product of glucose derivatives is used along with other water-soluble substances, it will mitigate the glow feel, sticky feel or the like which are causable by the presence of oil, thus the feel on use can be greatly improved. Ethyleneoxide adducts (10 to 30 mol E.O.) of methylglucoside are especially preferred for this purpose. Incorporation amount should be 1.0% or more based on the total weight of the liquid crystal composition for improving the feel on use.

The oil substances usable in this invention are any oils which are ordinarily used in cosmetic compositions, drugs and the like. Typical examples are hydrocarbons, esters of a higher alcohol and a higher fatty acid, fatty alcohols, fatty acids, triglycerides, oils or fats of animal and vegetable origin, cholesterol fatty acid esters, perfumes and the like, among which especially preferred are liquid paraffin, isostearylcholesteryl esters, glyceryl tri-2ethylhexanoate, octadecyl mirystate and olive oil. These are used singly or in combination. The incorporation amount is from 1 to 90%, preferably from 30 to 80% based on the total weight of the liquid crystal composition.

The amount of water may vary depending upon the use of the final product and the properties intended. Generally, water is incorporated 1 to 90%, preferably 5 to 30% based on the total composition.

The liquid crystal composition of this invention is prepared by blending a hydrophilic nonionic surfactant, a water-soluble substance having a hydroxyl group in a molecule thereof, an oil substance and water in such a range that will form a liquid crystal of a single phase. This preparation indicates Bragg space ratio of $1:\frac{1}{2}:\frac{1}{3}:\frac{1}{4}$ by the diffraction or low-angle scattering method of X-rays. Also, lamella texture is observed by the polarization microscope. Such a formulation is suitably determined based on the results of blending tests ordinarily carried out by experts skilled in the field. Points to which attention should be paid are the selection of the water-soluble substance, determination of its quantity and the blending ratio. The above parameters should be so determined that will maximize the molecular association of the surfactant when the liquid crystal is under formation.

In order to prepare the liquid crystal composition to be used as a substrate of the cosmetic composition of this invention, a hydrophilic nonionic surfactant, a water-soluble substance having a hydroxyl group in a molecule thereof, an oil substance, and water are blended at a higher temperature than a melting point of respective components to dissolve, then the mixture is cooled down to room temperature as it is stirred. Since a homogeneous liquid crystal is obtained in a single phase, as different from an emulsified composition consisting of two phases of dispersed phase and continuous phase, any order for blending the ingredients will lead to the same liquid crystal composition.

In order to obtain a good cosmetic composition comprising a liquid crystal as a substrate thereof, the liquid crystal can be prepared to have a formulation which follows:

Hydrophilic nonionic surfactant:
  Ethyleneoxide addition product of branched fatty alcohol, especially of Guerbet type having from 16 to 24 carbon atoms in total (E.O. addition: 10 to 30 mol)
  HLB: 10 to 40
  Amount: 10 to 20%
Water-soluble solvent:
  Polyol having three or more hydroxyl groups
  Amount: 5 to 15%
Oil substance:
  Liquid oil, especially ester oil
  Amount: 30 to 80%
Water:
  Amount: 5 to 30%
Ratio of water-soluble substance and water:
  1:4 to 4:1

Especially preferred liquid crystal composition of this invention is prepared when an ethyleneoxide addition product of Guerbet alcohol having HLB of 10 or more (hereinafter may be referred to as "Guerbet alcohol E.O. adduct") is used for a hydrophilic non-ionic surfactant, and a polyol having three or more hydroxyl groups is used for a water-soluble substance. In this case, example compounds of the usable Guerbet alcohol E.O. adduct are represented by the following formula (I):

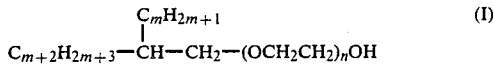

wherein m is a number from 6 to 10 and n is a number of 10 to 40.

Among the Guerbet alcohol E.O. adducts of formula (I), especially preferred is such that m is from 7 to 9, and n is from 20 to 30, and may be specifically referred to, for example, polyoxyethylene octyldodecyl ether (25 E.O.), polyoxyethylene heptylundecyl ether (20 E.O.), polyoxyethylene nonyltridecyl ether (30 E.O.).

Examples of the polyol having three or more hydroxyl groups are glycerine, diglycerine, polyglycerine, trimethylolpropane, erythritol, pentaerythritol, sorbitan, glucose, sorbitol, martitol, saccharose, trehalose, polyoxyethylene methyl glucoside, polyoxypropylene methyl glucoside, and the like. Among them, glycerine and sorbitol are especially preferred.

The oil-base cosmetic compositions comprising the liquid crystal composition according to the invention are prepared by adding pharmaceutical agents which are generally used in cosmetic compositions or drugs, preservatives, colorants, perfumes and the like as needed during or after a liquid crystal is formed.

When the lamella type, single phase liquid crystal composition according to the invention is applied to the skin, its chemical structure partially changes as the temperature is elevated because of the skin temperature, HLB value changes owing to water evaporation, and stress is incurred when spread on the skin. At this time, the oil substance will serve as a continuous phase and the highly associated hydrophilic nonionic surfactant will serve as a dispersed phase, so that the composition is softened or liquefied. When water is added, thereafter, the hydrophilic nonionic surfactant immediately turns to become a continuous phase, and the oil substance to a dispersed phase. This conversion takes place via a liquid crystal phase. Here, since the hydrophilic nonionic surfactant is oriented extremely densely to the interface between oil and water, the surface tention therebetween is lowered, thereby the oil substance is reduced into extremely small oil-in-water emulsion particles and thus readily removed from the skin surface by water.

Because the liquid crystal composition according to the invention is obtained in gel, it can be readily handled. Further, when it is applied to the skin, it is softened and then liquefied owing to the skin temperature. This feature is important for obtaining good feeling on use, especially in view of spreadability and smoothness, as well as for obtaining good permeability into the minute portions in the skin. Moreover, when water is added, the oil substance will turn into extremely minute oil-in-water particles, and will be readily removed from the skin. Accordingly, when the liquid crystal composition of this invention is used as a substrate of a cosmetic composition along with ordinary cosmetic ingredients or pharmaceutical agents, excellent cosmetic compositions or drugs for external application can be obtained, which have good storage stability, exhibit non-stickiness on use, have good spreadability and smoothness, and can be readily washed off with water.

The present invention will now be explained by way of examples, which should not be construed as limiting the invention.

EXAMPLE 1

Liquid crystal compositions shown in Table 1 were prepared according to the following process, on which the appearance, feel on use, consistency, storage stability and washability were examined. The results are also shown in Table 1.

Preparation

Ingredients (1) to (4) are heated to dissolve at 80° C. and mixed. The mixture is cooled down to room temperature while stirred to obtain liquid crystal compositions of the invention.

TABLE 1

| Liquid Crystal Composition | Inventive Products | | |
|---|---|---|---|
| | 1 | 2 | 3 |
| Composition (%) | | | |
| (1) Polyoxyethylene octyldodecyl ether (20 E.O.) | 10.0 | 15.0 | 20.0 |
| (2) Glyceryl tri-2-ethylhexanoate | 54.0 | 51.0 | 48.0 |
| (3) Glycerine | 25.2 | 23.8 | 22.4 |
| (4) Purified water | 10.8 | 10.2 | 9.6 |
| Ratio (2)/(3) + (4) | 1.5 | 1.5 | 1.5 |
| Characteristics | | | |
| Appearance | translucent flowable gel | transparent gel | transparent gel |
| Feeling on use | non-sticky, refreshing | non-sticky, refreshing | non-sticky, refreshing |
| Consistency (25° C.) | a little flowable | good | good |
| Storage stability (40° C., 1 month) | good | good | good |
| Washability | good | good | good |

EXAMPLE 2

Liquid crystal compositions shown in Table 2 were prepared according to the following process, on which the appearance, feel on use, consistency, storage stability and washability were examined. The results are also shown in Table 2.

Preparation

Ingredients (1) to (4) are heated to dissolve at 80° C. and mixed. The mixture is cooled down to room temperature while stirred to obtain liquid crystal compositions of the invention.

TABLE 2

| Liquid Crystal Composition | Inventive Products | | | | |
|---|---|---|---|---|---|
| | 4 | 5 | 6 | 7 | 8 |
| Composition (%) | | | | | |
| (1) Polyoxyethylene octyldodecyl ether (20 E.O.) | 20.00 | 20.00 | 20.00 | 20.00 | 20.00 |
| (2) Glyceryl tri-2-ethylhexanoate | 73.75 | 67.50 | 55.00 | 52.50 | 17.50 |
| (3) Glycerine | 5.00 | 10.00 | 20.00 | 30.00 | 50.00 |
| (4) Purified water | 1.25 | 2.50 | 5.00 | 7.50 | 12.50 |
| Ratio of water-soluble substance* | 0.8 | 0.8 | 0.8 | 0.8 | 0.8 |
| Characteristics | | | | | |
| Appearance | transparent gel | → | → | → | transparent flowable gel |
| Feeling on use | non-sticky, refreshing | → | → | → | → |
| Consistency (25° C.) | a little solid | good | → | → | a little flowable |
| Storage stability (40° C., 1 month) | good | → | → | → | → |
| Washability | good | → | → | → | → |

\* $\frac{(3)}{(3) + (4)}$

EXAMPLE 3

Liquid crystal compositions shown in Table 3 were prepared according to the following process, on which the appearance, feel on use, consistency, storage stability and washability were examined. The results are also shown in Table 3.

Preparation

Ingredients (1) to (4) are heated to dissolve at 80° C. and mixed. The mixture is cooled down to room temperature while stirred to obtain liquid crystal compositions of the invention.

TABLE 3

| Liquid Crystal Composition | Inventive Products | | | |
|---|---|---|---|---|
| | 9 | 10 | 11 | 12 |
| Composition (%) | | | | |
| (1) Polyoxyethylene octyldodecyl ether (20 E.O.) | 40 | 30 | 20 | 10 |
| (2) Glyceryl tri-2-ethylhexanoate | 40 | 50 | 60 | 70 |
| (3) Glycerine | 4 | 8 | 12 | 16 |
| (4) Purified water | 16 | 12 | 8 | 4 |
| Concentration of water-soluble substance* | 20 | 40 | 60 | 80 |
| Characteristics | | | | |
| Appearance | transparent gel | → | → | → |
| Feeling on use | non-sticky, refreshing | → | → | → |
| Consistency (25° C.) | a little solid | good | → | → |
| Storage stability (40° C., 1 month) | good | → | → | → |
| Washability | good | → | → | → |

*[(3)/(3) + (4)] × 100 (%)

EXAMPLE 4

Compositions shown in Table 4 were prepared according to the following process, on which the appearance, state of the liquid phase, feel on use at the equilibration, consistency, storage stability and washability were examined. The results are also shown in Table 4.

Preparation

For preparing Comparative Product A and the inventive product, the same process described in Example 1 was followed. Namely, ingredients (1) to (4) were heated to dissolve at 80° C. and mixed. The mixture was cooled down to room temperature while stirred to obtain the final compositions.

Comparative Product B was prepared following the process in which ingredient (1) was added into ingredient (3), heated to dissolve and mixed, to which ingredient (2) heated to 80° C. was added and mixed. Emulsion of oil-in-surfactant type was obtained in a gel state.

Ingredient (4) heated to 80° C. was further added and cooled down to room temperature while stirred to obtain the final composition.

Comparative Product A did not form a liquid crystal but form an emulsion when the oil phase, aqueous phase, and the surfactant were mixed simultaneously, thus turned out to have unacceptable stability against separation and washability. Comparative Product B, having the same composition as Comparative Product A, was obtained in gel when the ingredients were blended in a different order. This product exhibited good washability but gave unfavorable feel on use and separated soon. In contradistinction, the product according to the invention exhibited quite a good washability, good feel on use and long storage stability.

TABLE 4

|  | Comparative Product A | Comparative Product B | Inventive Product |
|---|---|---|---|
| Composition (%) |  |  |  |
| (1) Polyoxyethylene hydrogenated castor oil (50 E.O.) | 6 | 6 | 20 |
| (2) Liquid paraffin | 80 | 80 | 60 |
| (3) 1,3-butanediol | 7 | 7 | 10 |
| (4) Purified water | 7 | 7 | 10 |
| Preparation | (1)–(4) are heated to dissolve at 80° C. and mixed, then cooled down while stirred. | Mixture of (3) and (4) heated at 80° C. is added with (2) which is heated to dissolve, further added with (1). | (1)–(4) are heated to dissolve at 80° C. and mixed, then cooled down while stirred. |
| State |  |  |  |
| Appearance | turbid | gel | gel |
| Number of phase | 2 | 2 | 1 |
| Type | crystal | emulsion | Liquid crystal |
| Characteristics |  |  |  |
| Spreadability | non good | non good | good |
| Stickiness | non good | non good | good |
| Storage stability (40° C. 1 month) | separated | separated | good |
| Washability | non good | good | good |

EXAMPLE 5

Liquid crystal compositions shown in Table 5 were prepared according to the following process, on which the appearance, feel on use, consistency, storage stability and washability were examined. The results are also shown in Table 5.

Preparation

Ingredients (1) to (5) are heated to dissolve at 80° C. and mixed. The mixture is cooled down to room temperature while stirred to obtain a composition.

TABLE 5

| Liquid Crystal Composition | Inventive Product | Comparative Product |
|---|---|---|
| (1) Glyceryl tri-2-ethylhexanoate | 60 | 60 |
| (2) Polyoxyethylene octyldodecyl ether (20 E.O.) | 15 | — |
| (3) Polyoxyethylene octadecyl ether (20 E.O.) | — | 15 |
| (4) Glycerine | 18 | 18 |
| (5) Purified water | 7 | 7 |
| Appearance | transparent gel | translucent gel |
| Feeling on use | non-sticky, refreshing | oily feeling |
| Consistency (25° C.) | good | too flowable |
| Storage stability | good | separated |

TABLE 5-continued

| Liquid Crystal Composition | Inventive Product | Comparative Product |
|---|---|---|
| (40° C., 1 month) Washability | good | non good |

The comparative product containing a linear alcohol E.O. adduct is unhomogeneous because of insufficient gellation, whereas the product according to the invention containing a Guerbet alcohol E.O. adduct is homogeneous and reveals good storage stability. Further, because a phase transition readily takes place, it exhibits good feel on use and washability.

EXAMPLE 6

Massage Composition

All the following ingredients were heated to dissolve, mixed and then cooled down to prepare a single phase liquid crystal cosmetic composition.

| (Formulation) | |
|---|---|
| Glycerine | 10% |
| Propylene glycol | 1 |
| Polyoxyethylene sorbitan (30 E.O.) tetraoleate | 15 |
| Olive oil | 30 |
| Squalane | 30 |
| Dibutylhydroxytoluene | 0.1 |
| Methylparaben | 0.1 |
| Butylparaben | 0.1 |
| Perfume | 0.1 |
| Purified water | balance |

It gave smooth feel on use because it liquefied during the massage treatment, and was completely washed off by water after the treatment. It also revealed good storage stability.

EXAMPLE 7

Cleansing Composition

All the following ingredients were heated to dissolve, mixed and then cooled down to prepare a single phase liquid crystal cosmetic composition.

| (Formulation) | |
|---|---|
| Sorbitol | 10% |
| Polyoxyethylene methyl glucoside (10 E.O.) | 5 |
| Polyoxyethylene octyldodecyl ether (25 E.O.) | 15 |
| Glyceryl tri-2-ethylhexanoate | 60 |
| Dibutylhydroxytoluene | 0.1 |
| Methylparaben | 0.1 |
| Butylparaben | 0.1 |
| Perfume | 0.1 |
| Ethanol | 1 |
| Purified water | balance |

It was liquefied during the cleansing operation, so that the dirt in the minute portions in the skin was dispersed into the composition and readily washed off by water. The dirt removability was very good.

EXAMPLE 8

Drug Substrate

All the following ingredients were heated to dissolve, mixed and then cooled down to prepare a single phase drug substrate composition.

| (Formulation) | |
|---|---|
| Glycerine | 15% |
| Polyoxyethylene octyldodecyl ether (20 E.O.) | 15 |
| Squalane | 60 |
| Purified water | balance |

This composition can be combined with various kinds of oil-soluble drugs to prepare a drug.

What is claimed is:

1. A lamella type, single phase liquid crystal composition for cleansing human skin, comprising:
   (A) 10 to 20 wt % of one or more hydrophilic nonionic surfactants having an HLB value of 10 to 40,
   (B) 5 to 15 wt % of one or more water-soluble substances having at least one hydroxyl group,
   (C) 30 to 80 wt % of at least one oil substance which is liquid at normal temperature, and
   (D) 5 to 30 wt % of water.

2. A lamella type, single phase liquid crystal composition according to claim 1, wherein said hydrophilic non-ionic surfactant is an ethylene oxide addition product of Guerbet alcohol.

3. A lamella type, single phase liquid crystal composition according to claim 2, wherein said ethyleneoxide addition product of Guerbet alcohol is represented by the general formula (I):

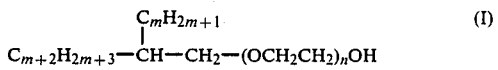

$$C_{m+2}H_{2m+3}\text{—}\overset{\overset{\displaystyle C_mH_{2m+1}}{|}}{CH}\text{—}CH_2\text{—}(OCH_2CH_2)_nOH \quad (I)$$

in which m is a number from 6 to 10, and n is a number from 10 to 40.

4. A lamella type, single phase liquid crystal composition according to claim 1, wherein said water-soluble substance is a polyol having three or more hydroxyl groups.

5. An oil base cosmetic composition comprising as a substrate thereof a lamella type, single phase liquid crystal composition which comprises:
   (A) 10 to 20 wt % of one or more hydrophilic nonionic surfactants having an HLB value of 10 to 40,
   (B) 5 to 15 wt % of one or more water-soluble substances having at least one hydroxyl group,
   (C) 30 to 80 wt % of at least one oil substance which is liquid at normal temperature, and
   (D) 5 to 30 wt % of water.

6. A lamella type, single phase liquid crystal composition according to claim 1, additionally containing an ethyleneoxide or propylene oxide addition product of a glucose.

7. A method of cleansing human skin which comprises:
   applying to the skin a lamella type, single phase liquid crystal composition for cleansing human skin, comprising:
   (A) 10 to 20 wt % of one or more hydrophilic nonionic surfactants having an HLB value of 10 to 40,
   (B) 5 to 15 wt % of one or more water-soluble substances having at least one hydroxyl group,
   (C) 30 to 80 wt % of at least one oil substance which is liquid at normal temperature, and
   (D) 5 to 30 wt % of water; and
   washing the skin with water to remove said lamella type, single phase liquid crystal composition.

* * * * *